United States Patent [19]
Tamura et al.

[11] Patent Number: 5,182,109
[45] Date of Patent: Jan. 26, 1993

[54] VACCINE PREPARATION COMPRISING A BACTERIAL TOXIN ADJUVANT

[75] Inventors: Shinichi Tamura, Kanagawa; Takeshi Kurata, Tokyo; Chikara Aizawa; Takashi Nagamine, both of Kanagawa, all of Japan

[73] Assignees: National Institute of Health; The Kitasato Institute, both of Tokyo, Japan

[21] Appl. No.: 335,678

[22] Filed: Apr. 10, 1989

[30] Foreign Application Priority Data

Apr. 8, 1988 [JP] Japan .................. 63-86693
Jan. 13, 1989 [JP] Japan .................. 1-6759

[51] Int. Cl.$^5$ .................. A61K 39/02; A61K 39/12
[52] U.S. Cl. .................. 424/92; 424/88; 424/89
[58] Field of Search .................. 424/92, 88, 89, 93

[56] References Cited

U.S. PATENT DOCUMENTS

| | | | |
|---|---|---|---|
| 4,440,748 | 4/1984 | Graham | 424/92 |
| 4,673,574 | 6/1987 | Anderson | 424/92 |
| 4,751,064 | 6/1988 | Sela et al. | 424/92 |
| 4,762,713 | 8/1988 | Anderson | 424/92 |
| 4,849,358 | 7/1989 | Chazono et al. | 424/92 |

FOREIGN PATENT DOCUMENTS

| | | |
|---|---|---|
| 0156633 | 10/1985 | European Pat. Off. . |
| 0175841 | 4/1986 | European Pat. Off. . |
| 8604243 | 7/1986 | PCT Int'l Appl. . |
| 1548787 | 7/1979 | United Kingdom . |

OTHER PUBLICATIONS

Schmeerson et al., *Infection and Immunity*, vol. 45, No. 3, pp. 582–591, Sep. 1984.
Armon et al., *Chemical Abstracts*, vol. 101, p. 479, Abstract No. 706662, 1984.
Tamura et al., *Biological Abstracts*, vol. 87, No. 1, Ref. No. 5274.

*Primary Examiner*—Johnnie R. Brown
*Assistant Examiner*—Abdel A. Mohamed
*Attorney, Agent, or Firm*—Young & Thompson

[57] ABSTRACT

A vaccine preparation comprising in combination a vaccine and a toxin or subunit thereof as an effective component. The toxin is preferably a bacterial toxin, e.g. cholera toxin, staphylococcal α-hemolysin, staphylococcal δ-hemolysin, vibrio thermostable direct hemolysin, pertussis toxin or *E. coli* heat-labile toxin. The toxin can be a B subunit or a part of a B subunit of a toxin. The vaccine can be influenza vaccine, pertussis vaccine, Japanese encephalitis vaccine, mixed vaccine of pertussis, diphtheria and tetanus toxoid, hepatitis B vaccine, rota vaccine, measles vaccine, rubella vaccine, mumps vaccine, combined vaccine of measles, rubella and mumps, or mycoplasma vaccine. The ratio of vaccine to toxin or subunit thereof is 1:0.0001–1:10,000 (w/v). The vaccine can be intranasal vaccine, or can be in injectable form, spray form or oral administration form.

7 Claims, 3 Drawing Sheets

VACCINE PREPARATION COMPRISING A BACTERIAL TOXIN ADJUVANT

FIELD OF THE INVENTION

This invention relates to a vaccine preparation. More particularly the present invention relates to a vaccine preparation comprising a toxin or subunit thereof as an effective ingredient.

THE PRIOR ART

Vaccines have been used for protection against various kinds of diseases and have provided good results. However, side reactions or insufficient effectiveness of vaccines have sometimes been observed and hence there has been a strong demand for their improvement. To reduce the side reactions of vaccines, it has been attempted to prepare more highly purified vaccines or to administer smaller amounts of vaccine. However, these efforts have only resulted in less effectiveness of the vaccine.

At present, various vaccines for human therapy have been prepared from pathogens or components thereof. Therefore the contamination of components which comprise pathogens, or the medium which is used for culturing the pathogens, in a vaccine cannot be avoided; and this induces side effects of vaccine inoculation.

The development of effective vaccines is accordingly needed, with augmented immunological potency but without side effects.

In order to achieve this, a decrease in the inoculum size of the vaccine and a change in the route of administration have been tried.

BRIEF SUMMARY OF THE INVENTION

We have found that an enhancement of the immune potency of a vaccine can be achieved by administering a vaccine together with a bacterial toxin, especially cholera toxin, Staphylococcal α-hemolysin, Staphylococcal δ-hemolysin, Vibrio thermostable direct hemolysin, pertussis toxin or *E. coli* heat-labile toxin, or a subunit thereof.

OBJECTS OF THE INVENTION

An object of the present invention is to provide a vaccine preparation which has enhanced immunological potency with decreased dosage.

Another object of the present invention is to provide a vaccine preparation comprising a toxin or subunit thereof as an effective ingredient.

A further object of the present invention is to provide a vaccine preparation containing a bacterial toxin.

A still further object of the present invention is to provide a vaccine preparation containing a bacterial toxin selected from the group consisting of cholera toxin, Staphylococcal α-hemolysin, Staphylococcal δ-hemolysin, Vibrio thermostable direct hemolysin, pertussis toxin or *E. coli* heat-labile toxin.

Another object of the present invention is to provide a vaccine preparation in which the subunit of a toxin is a B subunit.

A still further object of the present invention is to provide a vaccine selected from the group consisting of influenza, pertussis vaccine, diphtheria and tetanus toxoid combined with pertussis vaccine, Japanese encephalitis vaccine, hepatitis B vaccine, rota vaccine, measles vaccine, rubella vaccine, mumps vaccine, a mixed vaccine of measles, rubella and mumps, and mycoplasma vaccine.

Still another object of the present invention is to provide a vaccine preparation consisting of a ratio of vaccine and toxin or subunit thereof of 1:0.0001–1:10,000 (w/v%).

Another object of the present invention is to provide a vaccine preparation comprising an intranasal vaccine.

Finally, it is an object of the present invention to provide a vaccine preparation which is in injectable form, spray form or oral administration form.

DETAILED DESCRIPTION OF THE INVENTION

Influenza vaccine as an example of vaccine and cholera toxin (hereinafter CT) and cholera toxin B subunit (hereinafter CTB) as an example of bacterial toxin are exemplified for illustrating the present invention.

We have studied cholera toxin, a protein endotoxin produced by Vibrio cholera as a local immunomodulator against vaccine administered intranasally. Cholera toxin is an effective intestinal immunogen and is responsible for diarrhea in cholera. Moreover, it is known not only as an effective immunogen which induces IgA antibody production, but also as an immunomodulating agent which stimulates the immune responses to simultaneously administered unrelated protein antigens, when CT and the unrelated antigen are administered simultaneously. The effect of CT has been defined as an action which increases intra-cellular cAMP level in the intestinal mucosal cells. The mechanism of action of CT, which is composed of an A subunit and a B subunit, is that CTB binds to $GM_1$ ganglioside in a cell membrane, and the A subunit which enters into the cell and activates adenylate cyclase. CTB, the nontoxic component of CT, is also known as a gut mucosal immunogen when administered simultaneously with unrelated protein antigens. These facts suggest that both CT and CTB can act on the respiratory mucosa, as well as on the intestinal mucosa, to stimulate the local immune responses to unrelated coexisting antigens.

We have examined the effectiveness of CT and CTB as an adjuvant for local and serum antibody production for nasal vaccination of mice by using influenza HA vaccine (hereinafter HA vaccine). Also the usefulness of CT and CTB as adjuvants for vaccination was examined.

Increased Vaccination Effect of CTB for Nasal Vaccination By Using HA Vaccine on Immunoresponse The effects of CTB on antibody responses to HA vaccine (A/Yamagata) were investigated in mice which received the vaccine together with CTB intranasally.

Simultaneously, the results of intranasal administration were compared with those of the other inoculation routes.

Four weeks after the nasal vaccination, which was effected by dropping HA vaccine (2 μg) alone or together with CTB (5 μg) intranasally in mice (or administering it intraperitoneally or subcutaneously), hemagglutinin-inhibiting (hereinafter HI) antibody levels in the serum and influenza specific IgA antibody (hereinafter anti HA-IgA antibody) and CTB specific IgA antibody (hereinafter anti CTB-IgA antibody) in nasal wash were assayed.

As shown in Table 2 hereafter, a control group of mice which received only the HA vaccine intranasally produced only a low level of serum HI antibodies. Nasal inoculation of CTB together with HA vaccine led to a 64-fold higher level of serum HI antibodies. Anti-HA-IgA and anti-CTB-IgA antibodies in the nasal wash were also observed. Intraperitoneal or subcutaneous inoculation of HA vaccine alone induced a high level of serum HI antibody, and the inoculation of HA vaccine together with CTB induced a 4–8 times higher level of serum HI antibodies. However neither detectable nasal anti-HA-IgA nor anti-CTB-IgA antibodies were produced.

As a result, it has been found that CTB is an effective adjuvant which stimulates nasal anti-HA-IgA antibody production when administered intranasally together with HA vaccine.

Although it is not shown in Table 2, no serum anti-HA-IgA was detected.

Effect of CTB on Primary Antibody Response to HA Vaccine After Intranasal Administration The progress of antibody production in mice which received intranasally HA vaccine (A/Yamagata, 2 μg) together with CTB (5 μg) was examined.

Figure 1A:
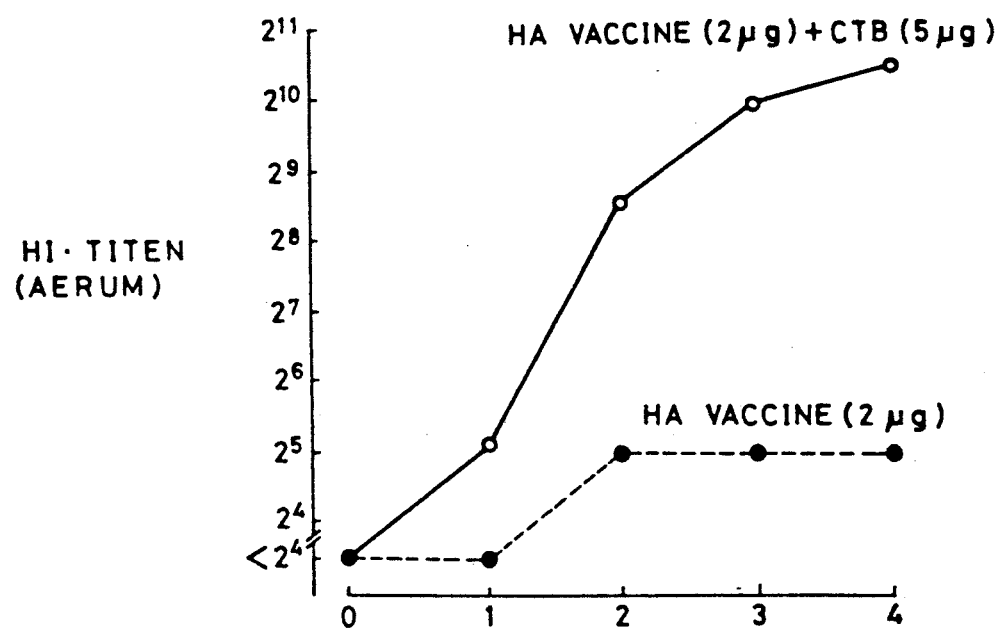
FIG. 1A is a graph sowing HI antibody production in the first four weeks after administering a vaccine of the present invention.
Figure 1B:
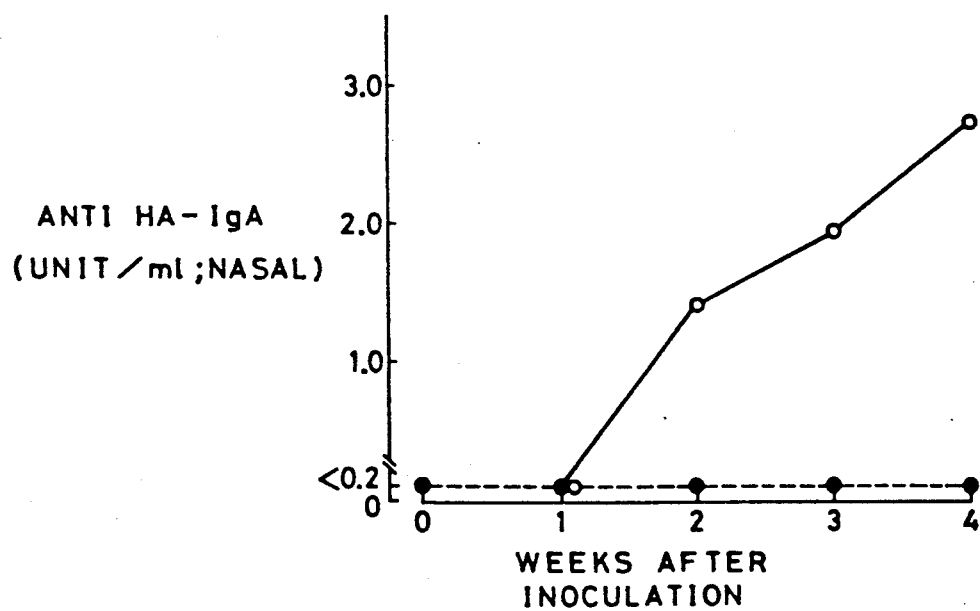
FIG. 1B is a graph corresponding to that of FIG. 1A, showing the amount of anti HA-IgA production.
Figure 1C:
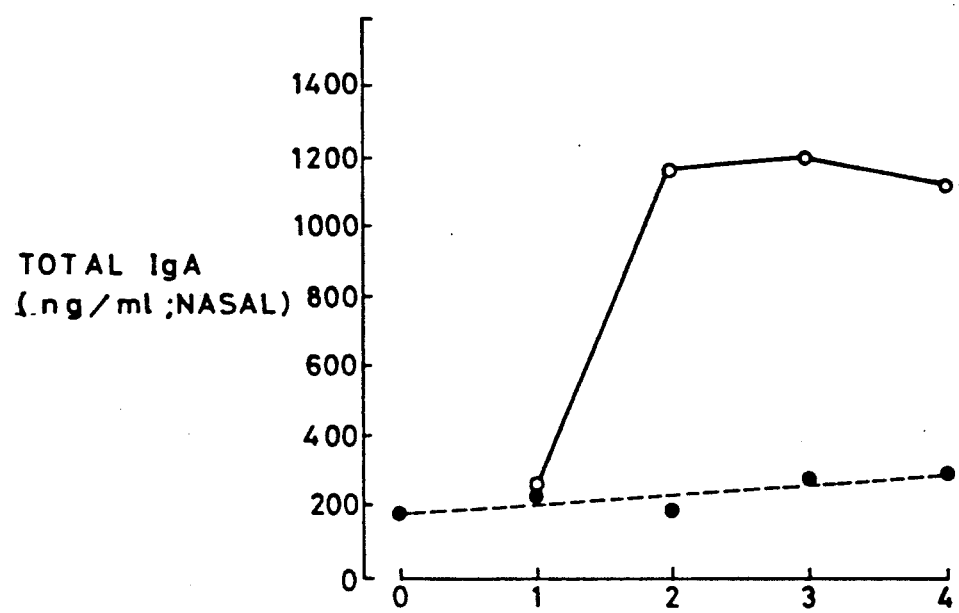
FIG. 1C is a graph corresponding to that of FIG. 1A, showing the total amount of IgA in the nasal wash.
Figure 1D:
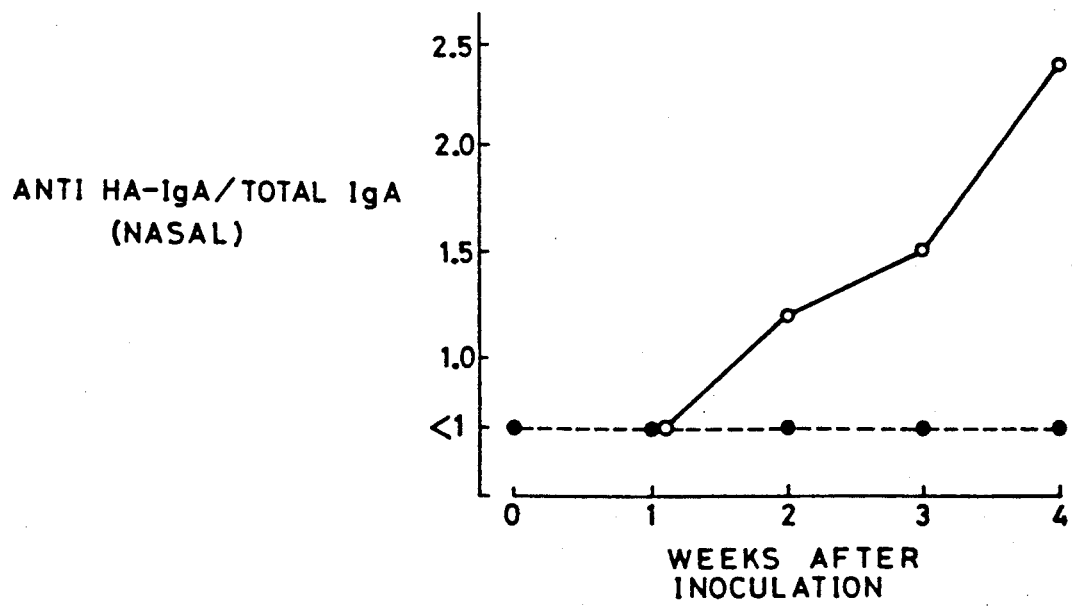
FIG. 1D is a graph corresponding to that of FIG. 1A, showing the amount of anti HA-IgA as a function of the total IgA.

As shown in FIG. 1A, HI antibody production for serum vaccine together with CTB rapidly increased during 1 to 2 weeks, and thereafter it increased gradually until 4 weeks. The total amount of IgA in the nasal wash rapidly increased to a maximum level after 1 to 2 weeks of inoculation and was approximately six times as high as that in the control group. The amount of anti HA-IgA therein gradually increased after 1 week to 4 weeks.

Anti-HA antibodies in the nasal wash began to be detectable approximately 2 weeks after administering both CTB and vaccine.

Effect of CTB on Primary and Secondary Antibody Responses to HA Vaccine

The effect of CTB (5 μg) and various amounts of HA vaccine (A/Yamagata) on anti-HA antibody response were investigated.

Primary antibody production was investigated in mice, which received a primary intranasal inoculation of the various doses of HA vaccine together with CTB, after 4 weeks of inoculation, then secondary antibody production was detected another 2 weeks later in mice, which received the second intranasal inoculation of HA vaccine (2 μg) alone.

As shown in Table 3, a low level of primary antibody production was observed even at 8 μg of HA vaccine inoculation alone. On the other hand, both nasal anti-HI-IgA antibody and serum HI antibody increased with an increase in the intranasal dose of HA vaccine even at 0.03 μg of inoculation, when CTB was administered concomitantly. Furthermore, in mice which received the second intranasal inoculation of HA vaccine alone after the primary inoculation, the level of anti-HI and anti-HA-IgA antibodies production was enormously elevated, and was independent of the primary HA vaccine dose inoculated with CTB. Mice which received a primary inoculation of CTB and HA vaccine showed extremely high levels of anti-HI and anti-HA-IgA antibodies production, and this was independent of the amount of primary HA vaccine inoculation. In particular, the level of nasal anti-HA-IgA antibody was about 50–100 times as high as that after primary inoculation. These results show that the primary inoculated CTB strongly stimulates antibody production upon secondary inoculation without regard to the amount of HA vaccine. Namely, CTB can effectively produce an immunological memory for the production of nasal IgA antibodies by HA vaccine at relatively low concentrations.

Effects of CTB on Augmentation of Immune Response and Protection of Mice Against Influenza Virus Infection The immunological response against HA vaccine was augmented by concomitantly administered CTB in mice. The effectiveness of CTB as an adjuvant was tested by production experiments using mouse adapted influenza virus, strain PR8. Mice were inoculated intranasally with both the PR8 HA vaccine (1.5 μg) and CTB (5 μg), and 4 weeks later, infected intranasally with PR8 virus. Three days after infection, pulmonary virus titers were determined as an index of protection. As shown in Table 4, complete protection against the challenge infection with no detection of virus in the lungs of mice was provided by the inoculation of vaccine with CTB and the production of high levels of both serum HI antibodies and nasal anti-Ha-IgA antibodies in mice, and none of the mice were infected.

In order to confirm the pulmonary virus titer after 3 days of viral infection as an indicator of resistance to infection against viral infection in mice, mice were inoculated with both HA vaccine and CTB, and 4 weeks later, inoculated intranasally with virus strain PR8. After infection, the variation of pulmonary virus titers was determined.

Figure 2:
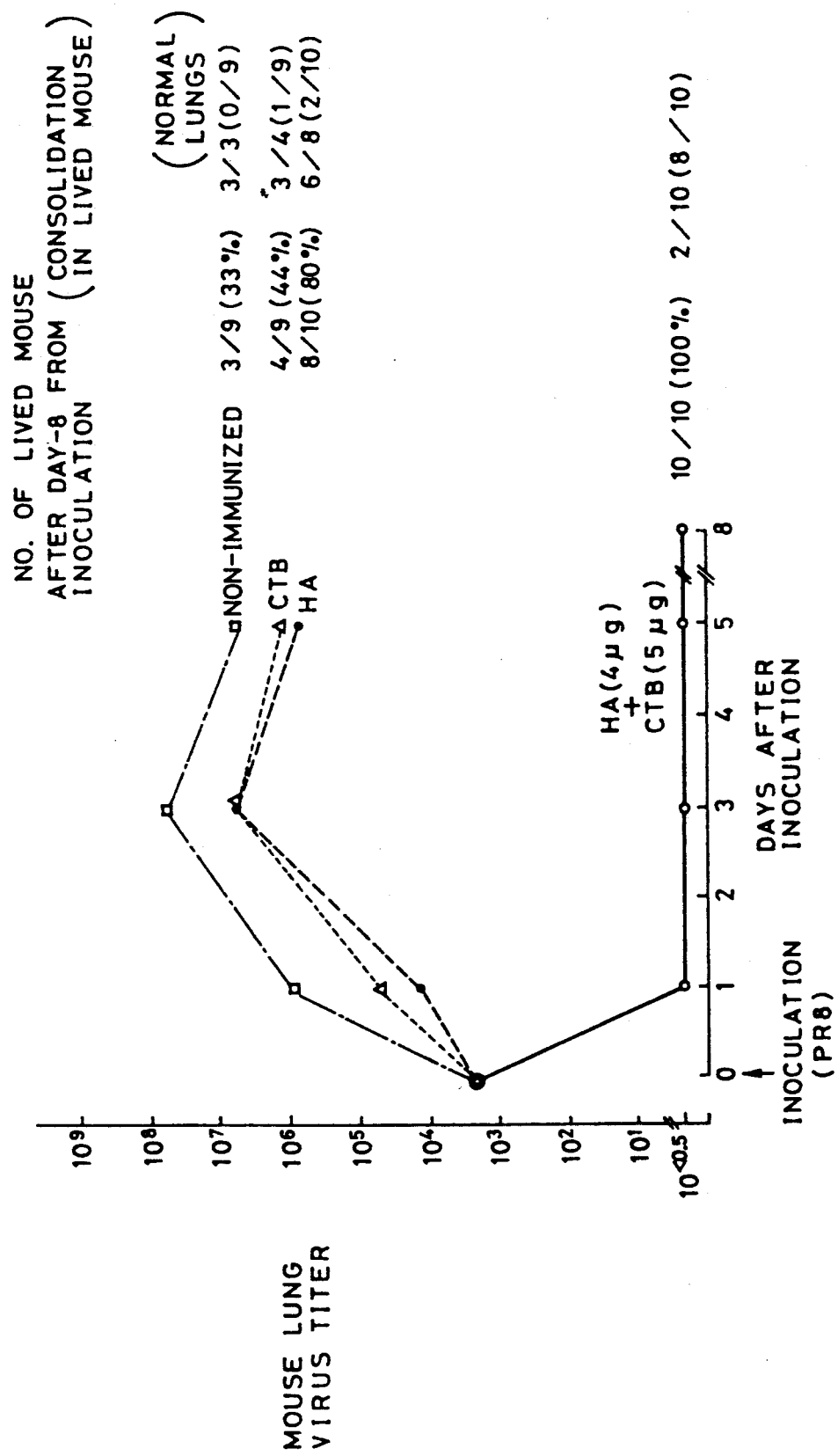
FIG. 2 is a graph of infections lesions in the lung after administering a vaccine of the present invention.

As illustrated in FIG. 2, mice which were observed to have pulmonary virus $<10^{0.5}$ after 3 days of infection, showed no detectable virus one day after infection and maintained a diminished level with survival thereafter at least 8 days. On the contrary, the lungs of mice in the control groups, which failed to produce detectable protective antibodies, showed evidence of infection which began to increase one day after infection and reached its maximum after 3 days. Death of mice in the control group was observed after 6 days of infection and in the non-immunized group 6 of 9 mice died after 8 days. The surviving 3 mice showed severe lesions in the lungs and were judged to die within a few days. Similar results as in the non-immunized group were observed in mice inoculated with HA vaccine or CTB alone. It is concluded that the pulmonary virus titer after 3 days of infection can be used as an indicator of resistance to infection.

Effect of Dosage of CTB or CT on the Augmentation of Immune Response and Protection of Mice Against Influenza Virus Infections The effect of CT or CTB dosage, inoculated intranasally with the PR8 HA vaccine (1.5 μg), on protection against PR8 virus challenge and antibody production were investigated. As shown in Table 5, a slight resistance to infection with a dose of CTB (0.05 μg) was observed, and complete protection against the challenge infection was provided by the inoculation of vaccine with 5 μg of CTB. The degree of resistance to infection seems to be directly proportional to the level of anti-Ha-IgA antibodies in the nasal wash and the level of HI antibodies in the serum 4 weeks after the inoculation of vaccine with CTB.

Complete protection to infection was observed at levels of CT more than 0.05 μg, and under these conditions, the increase of HI antibodies in the serum and anti-HA-IgA antibodies in the nasal wash was observed according to the increase in the level of CT.

These results suggest that CT is ten or more times more effective than CTB, on a dosage basis, to increase HI antibodies production in the serum and anti-Ha-IgA antibodies production in the nasal wash necessary for protection against infection.

CT can be used as an effective adjuvant at low dosage levels as compared with CTB, if there are no side effects.

It appears that HI antibodies more than 32 times antibody titers in serum, and local antibodies more than 2 units of anti-HA-IgA antibodies are required for complete protection against PR8 virus infection.

In Table 1, the adjuvant activities of various bacterial toxins are illustrated.

TABLE 1

| Toxins | Inoculum size Toxin (μg/mouse) | Influenza HA (μg/mouse) | Antibody production HI($2^n$) | No. of mice survived/treated |
|---|---|---|---|---|
| Staphylococcal α-hemolysin | 0.5 | 1.5 | 10.0 ± 1.7 | 5/5 |
| Staphylococcal δ-hemolysin | 5 | 1.5 | <4 | 5/5 |
|  | 0.5 | 1.5 | <4 | 5/5 |
| Vibrio thermostable direct hemolysin | 5 | 1.5 | 11.5 | 5/5 |
|  | 0.5 | 1.5 | 9.8 ± 1.1 | 5/5 |
| E. coli heat-labile toxin (LT) | 5 | 1.5 | 11.8 ± 0.4 | 5/5 |
|  | 0.5 | 1.5 | 10.8 ± 2.2 | 5/5 |
| Pertussis toxin | 5 | 1.5 | 11.6 ± 0.5 | 5/5 |
|  | 0.5 | 1.5 | 10.2 ± 1.7 | 5/5 |
| Control | 0 | 1.5 | <4 | 0/5 |
|  |  |  | <4 | 0/5 |

TABLE 2

Augmentation of antiviral antibody response to influenza HA vaccine (A/Yamagata) by CTB

| Group No. | Inoculation Material HA vaccine (2 μg) | CTB (5 μg) | Route | Antibody Responses (4 weeks) Serum HI titer ($2^n$) | Nasal IgA AntiHA-IgA (units) | AntiCTB-IgA (units) |
|---|---|---|---|---|---|---|
| 1 | — | — | — | $<2^4$ | <0.2 | <0.2 |
| 2 | — | + | Intranasal | $<2^4$ | <0.2 | 8.3 ± 0.3 |
| 3 | + | — | Intranasal | $2^5$ | <0.2 | <0.2 |
| 4 | + | + | Intranasal | $2^{11}$ | 3.3 ± 0.3 | 7.4 ± 1.1 |
| 5 | + | — | Intraperitoneal | $2^8$ | <0.2 | <0.2 |
| 6 | + | + | Intraperitoneal | $2^{11}$ | <0.2 | 0.2 |
| 7 | + | — | subcutaneous | $2^8$ | <0.2 | <0.2 |
| 8 | + | + | subcutaneous | $2^{10.5 \pm 0.7}$ | <0.2 | 0.2 |

TABLE 3

Augmentation of primary and secondary antiviral antibody responses by nasal inoculation of influenza HA vaccine together with CTB

| Group No. | primary Nasal Inoculation HA (μg) | CTB (5 μg) | Antibody Responses after 4 weeks (primary) Serum HI antibody (units) | Nasal AntiHA-IgA (units) | Antibody Response after 2 weeks Secondary (2 μg HA vaccine) Serum HI antibody (units) | Nasal AntiHA-IgA (units) |
|---|---|---|---|---|---|---|
| 1 | — | — | $<2^4$ | <0.2 | $2^5$ | <0.2 |
| 2 | — | + | $<2^4$ | <0.2 | $2^{3.5 \pm 0.7}$ | 1.2 ± 1.2 |
| 3 | 0.03 | — | $<2^4$ | <0.2 | $2^8$ | 2.9 ± 1.6 |
| 4 | 0.5 | — | $<2^4$ | <0.2 | $2^{0.5 \pm 0.7}$ | 2.6 ± 0.6 |
| 5 | 8 | — | $2^5$ | 0.3 ± 0.1 | $2^{8.5 \pm 0.7}$ | 4.5 ± 2.1 |
| 6 | 0.03 | + | $2^6$ | 0.7 ± 0.3 | $2^{12.5 \pm 0.7}$ | 60 ± 4 |
| 7 | 0.5 | + | $2^{0.5 \pm 0.7}$ | 2.5 ± 0.4 | $2^{12.5 \pm 0.7}$ | 113 ± 27 |
| 8 | 8 | + | $2^{11.5 \pm 0.7}$ | 4.6 ± 0.3 | $2^{12.5 \pm 0.7}$ | 78 ± 10 |

TABLE 4

Protection against infection with influenza virus (PR8) inoculated with HA vaccine and CTB

| Group No. | Nasal Inoculation HA vaccine (1.5 μg) | Nasal Inoculation CTB (5 μg) | Antiviral antibodies after 4 weeks of inoculation Serum HI antibody ($2^n$) | AntiHA-IgA (units) | Mouse lung titer after 3 days infection $EID_{50}$ ($10^n$) | Incidence of infection (%) |
|---|---|---|---|---|---|---|
| 1 | − | − | $<2^4$ | <0.2 | $10^{6.8} \pm 0.5$ | 5/5 (100) |
| 2 | − | + | $<2^4$ | <0.2 | $10^{7.1} \pm 0.5$ | 5/5 (100) |
| 3 | + | − | $<2^4$ | <0.2 | $10^{5.7} \pm 0.5$ | 5/5 (100) |
| 4 | + | + | $2^{7.3} \pm 1.3$ | 4.6 ± 0.7 | $10^{<0.5}$ | 0/5 (0) |

TABLE 5

Effect of CTB or CT dose on protection against infection

| Group No. | Nasal Inoculation HA vaccine (1.5 μg) | Nasal Inoculation CTB (CT) (μg) | Antibody Responses (4 weeks after inoculation) Serum HI antibody titer ($2^n$) | Nasal AntiHA-IgA (units) | Nasal AntiCTB-IgA (units) | Mouse lung after 3 days infection ($ED_{50}$) ($10^n$) |
|---|---|---|---|---|---|---|
| 1 | − | − | $<2^4$ | <0.2 | <0.2 | $10^{6.8}$ |
| 2 | − | CTB (5) | $<2^4$ | <0.2 | 6.2 ± 1.3 | $10^{7.1}$ |
| 3 | + | − | $<2^4$ | <0.2 | <0.2 | $10^{5.7}$ |
| 4 | + | CTB (0.05) | $<2^4$ | 0.5 | <0.2 | $10^{3.9}$ |
| 5 | + | CTB (0.5) | $2^{4.5} \pm 0.7$ | 1.2 ± 0.9 | 1.5 ± 1.0 | $10^{2.5}$ |
| 6 | + | CTB (5) | $2^{0.5} \pm 0.7$ | 4.6 ± 0.7 | 3.7 ± 0.6 | $10^{<0.5}$ |
| 7 | + | CT (0.05) | $2^5$ | 2.0 ± 0.8 | <0.2 | $10^{<0.5}$ |
| 8 | + | CT (0.5) | $2^7$ | 3.2 ± 0.6 | 0.6 ± 0.6 | $10^{<0.5}$ |
| 9 | + | CT (5) | $2^{8.5} \pm 0.7$ | 3.1 ± 0.1 | 2.7 ± 0.1 | $10^{<0.5}$ |

As hereinabove illustrated, the following facts have been found:

(1) Administration of influenza HA vaccine together with CT or CTB augments the immunological production.

(2) Augmentation of the serum HI antibodies production and local intranasal anti-HA-IgA production are augmented by the intranasal inoculation of HA vaccine with CTB. Almost no local intranasal HA-IgA antibodies production is observed when inoculated intraperitoneally and subcutaneously, but the high level of antibodies production in the serum is found.

As a result, CTB has an augmentation activity as to antibody production by any inoculation route.

This means that the mixed administration of CT, CTB, Staphylococcal α-hemolysin, Staphylococcal δ-hemolysin, Vibrio thermostable direct hemolysin, pertussis toxin or E. coli heat-labile toxin with pertussis vaccine, diphtheria and tetanus toxin combined with pertussis vaccine, hepatitis B vaccine, Japanese encephalitis vaccine, measles vaccine, rubella vaccine, mumps vaccine, measles, rubella and mumps mixed vaccine, rota vaccine or mycoplasma vaccine shows a high level of titer as compared with that of a single dose of vaccine.

In other words, the inoculum size of the vaccine can be reduced by administering it together with a toxin or a subunit thereof.

(3) The level of local nasal anti-HA-IgA antigen is increased over 2 to 4 weeks by intranasally inoculating a vaccine with CTB.

(4) Antibody production 4 weeks after intranasal inoculation of vaccine with CTB is proportional to the dosage level of the inoculated vaccine.

(5) In mice which received the second intranasal inoculation of the vaccine alone, 4 weeks after the primary inoculation of the vaccine with CTB, the level of secondary antibody production 2 weeks after the second inoculation was enormously elevated, and was independent of the primary vaccine dose inoculated with CTB. Therefore, CTB can effectively produce an immunological memory.

(6) Complete protection against influenza virus infection was provided by the intranasal inoculation of vaccine with CTB in mice, in which the production of high levels of both serum antibody titers and nasal anti-HA-IgA antibodies was observed.

Under the present experimental conditions, in mice which maintain serum HI antibodies more than 32 times the antibody titers and local nasal antibodies more than 2 units, complete protection against PR8 virus infection was achieved.

(7) The inoculum size of CTB necessary for induction of antibody production for complete protection to infection, intranasally inoculated with vaccine, is on the order of 5 μg. CT can induce antibody production which requires for complete protection to infection a level below 1/10 as much CTB.

Toxins or subunits thereof used in the present invention, such as CT or CTB, can be prepared by the known procedures, and are also commercially available. CT is toxic when administered in a large amount but is nontoxic when intranasally or intraperitoneally inoculated. CTB is less toxic than CT and presents no problem upon intranasal administration. Examples of further toxins are Staphylococcal α-hemolysin, Staphylococcal δ-hemolysin, Vibrio thermostable direct hemolysin, pertussis toxin and E. coli heat-labile toxin.

Examples of vaccines are influenza vaccine, pertussis vaccine, diphtheria and tetanus toxoid combined with pertussis vaccine, hepatitis B vaccine, Japanese encephalitis vaccine, measles vaccine, rubella vaccine, mumps vaccine, mixed vaccine of measles, rubella and mumps, rota vaccine and mycoplasma vaccine, and others. These can be produced by known common processes. Their production is illustrated as follows:

Influenza vaccine: a vaccine comprising the whole or a part of hemagglutinin (HA), neuraminidase (NA), nucleoprotein (NP) and matrix protein (M) which are obtainable by purifying a virus, which is grown in embryonated eggs, with ether and detergent, or by genetic engineering techniques or chemical synthesis.

Pertussis vaccine: a vaccine comprising the whole or a part of pertussis toxin (PT), hemagglutinin (FHA) and K-agglutin which are obtained from avirulent toxin with formalin which is extracted by salting-out or ultracentrifugation from the culture broth or bacterial cells of Bordetella pertussis, or by genetic engineering techniques or chemical synthesis.

Diphtheria and tetanus toxoid combined with pertussis vaccine: a vaccine mixed with pertussis vaccine, diphtheria and tetanus toxoid.

Japanese encephalitis vaccine: a vaccine comprising the whole or a part of an antigenetic protein which is obtained by culturing a virus intracerebrally in mice and purifying the virus particles by centrifugation or ethyl alcohol and inactivating the same, or by genetic engineering technique or chemical synthesis.

Hepatitis B vaccine: a vaccine comprising the whole or a part of an antigen protein which is obtained by isolating and purifying the HBs antigen by salting-out or ultracentrifugation, obtained from hepatitis B carrying blood, or by genetic engineering or chemical synthesis.

Measles vaccine: a vaccine comprising the whole or a part of a virus grown in cultured chick embryo cells or embryonated egg, or a protective antigen obtained by genetic engineering technique or chemical synthesis.

Rubella vaccine: a vaccine comprising the whole or a part of a virus grown in cultured chick embryo cells or embryonated egg, or a protective antigen obtained by genetic engineering technique or chemical synthesis.

Mumps vaccine: a vaccine comprising the whole or a part of a virus grown in cultured rabbit cells or embryonated egg, or a protective antigen obtained by genetic engineering technique or chemical synthesis.

Mixed vaccine of measles, rubella and mumps: a vaccine produced by mixing measles, rubella nd mumps vaccines.

Rota vaccine: a vaccine comprising the whole or a part of a virus grown in cultured MA 104 cells, or isolated from patients's feces, or a protective antigen obtained by genetic engineering technique or chemical synthesis.

Mycoplasma vaccine: a vaccine comprising the whole or a part of mycoplasma cells grown in a liquid culture medium for mycoplasma, or a protective antigen obtained by genetic engineering technique or chemical synthesis.

The above illustrated vaccines are provided in liquid or powdered form.

The liquid form of the vaccine is preferable for intranasal administration such as by intranasal spray, or nose drops, or applying or injection together with a toxin or a subunit thereof. Powder spraying intranasally can also be used. The amount of the dose may be 5 $\mu$l–50 $\mu$l intranasally in mice and is preferably 0.1–0.5 ml for intranasal spray application or injection in humans. These amounts of administration can also be modified accordingly.

The mixture ratio of the vaccine to the toxin or its subunit is 1:0.001–1:10,000 (w/v%) and depends on the amount of dosage in humans.

The vaccines of the present invention can be prepared by mixing the above illustrated vaccines with toxins or subunits thereof at a desired ratio. The preparation should be conducted strictly aseptically, and each component should also be aseptic. Pyrogens or allergens should naturally be removed as completely as possible.

The vaccine preparation of the present can be used by preparing the vaccine per se and the toxin or subunit thereof separately and mixing the two before inoculation, or by inoculating each separately.

The following examples illustrate the vaccine the present invention comprising influenza vaccine and CT CTB and the effects thereof.

EXAMPLE 1

Animal: Female Balb/c mice, 6 to 8 weeks old.

HA vaccine: HA vaccines were prepared from influenza virus by treatment with ether to remove the lipids. HA component of approximately 30% is contained in the vaccine. The inoculum sizes shown in Tables 2-5 expressed as the amount of HA.

CT and CTB: Cholera toxin (CT) and its B subunit (CTB) were purchased from Sigma Chemical Co., U.S.A. The CTB preparation used in the present experiments did not reveal any detectable contamination with A subunit as determined by SDS-polyacrylamide gel electrophoresis.

Immunization

A vaccine preparation was prepared by diluting HA vaccine or adjuvant with phosphate-buffered saline (PBS). Mice were anaesthetized by an intraperitoneal injection of sodium amobarbital and then immunized by an intranasal dripping inoculation of 20 μl of the vaccine preparation. Alternatively they were immunized by a subcutaneous or an intraperitoneal injection of 100 μl of the vaccine.

Serum and Nasal Washed Specimens

Serum specimens were collected from mice by drawing whole blood from their heart. Nasal wash specimens were obtained by washing the nasal cavities twice with a total of 1 ml PBS.

Hemagglutination Inhibition (HI) Test

Serum for HI titer assay was prepared after removal of non-specific inhibitors by a receptor-destroying enzyme (RED). The serum was diluted 2-fold on a U-type microtiter plate and mixed with 16 HA units of virus, which were allowed to stand for 30 minutes at room temperature. Then chick red cells were added thereto for assaying.

The results were determined after standing at room temperature for 1 hour.

Assay of Anti-HA-IgA, Anti-CTB-IgA and Total IgA

Antiviral IgA, anti-CTB antibodies and total IgA in the nasal wash and serum were measured by ELISA. The wells of a 96-well EIA plate (half-acre, Costar, Cambridge, MA) were coated with either 50 μl of HA vaccine (5 μg/ml) or CTB (5 μg/ml). The plate was incubated for 2 hours at room temperature and then washed three times with PBS-Tween. The PBS solution (100 μl) containing 1% bovine serum albumin (BSA) and 0.1% $NaN_3$, was placed in the wells for coating, and incubated overnight at 4° C. After washing with PBS-Tween, each sample of either serum or nasal wash was added to the wells. The plates were incubated for 2 hours at room temperature and washed with PBS-Tween.

Alkaline-phosphatase-coupled goat anti-mouse IgA (α-chain specific, 1:1000, Zymed Laboratories, Inc. U.S.A., 50 μl) was added to each well. The plate was incubated at room temperature for 1 hour and then washed with PBS-Tween. Finally p-nitrophenylphosphate (1 mg/ml, Sigma Co.) in 10% diethanolamine buffer at pH 9.8 (100 μl) was added to each well.

After 20-30 mins. the absorbance of the plates was read at 410 nm ($OD_{410}$) in a SJeia Auto Reader (Model ER-8000, Sanko Junyaku Co., Tokyo). A standard curve was prepared for each plate. A standard regression curve, which is transformed by a logic-log equation, was constructed for each assay and the unknowns were interpolated using a program on the SJeia Auto Reader.

A standard anti-HA-IgA measurement solution is defined as an 8-unit standard for antiviral IgA antibodies, comprising nasal specimens from mice which receive 5-times repeated nasal inoculations of the HA vaccine at 2-week intervals. A standard anti-CTB-IgA measurement solution is defined as an 8-unit standard for antiviral IgA antibodies, comprising nasal specimens from mice 4 weeks after the nasal inoculations of CTB (5 μg).

Total IgA was determined by the same way as illustrated hereinabove except that the goat anti-mouse IgA (50 μl, 1 μg/ml) was added to each well. Mouse purified IgA myeloma (Miles Labs. U.S.A.) was used as a standard solution for total IgA measurement.

Infection with PR8 Virus in Mice

Mice were anesthetized and then infected by intranasal dropping administration of 20 μl of a virus suspension containing 0.01% BSA into the left nasal cavity. The virus suspension was prepared as a 1/5000-1/10000 suspension of an original virus pool with $10^{8.5}$ $EID_{50}$ which was prepared by inoculating 148 transfers in ferrets, 72 transfers in mice and 72 transfers in embryonated eggs. In this infectious condition, more than 90% of those non-immunized died within 14 days or formed consolidations in the lungs.

Virus Titrations in the Lung

Three days after infection, the lungs of mice were removed, homogenized to give a 10% suspension in PBS and then centrifuged at 2500 rpm. Serial dilutions (1:10) of the supernatant of individual lung homogenates were prepared and each dilution was injected into 5 embryonated eggs. The lung virus titer of each mouse was determined by the hemagglutinating capacity of the allantoic fluid and expressed by the lowest dilution of lung homogenate with $EDI_{50}$ in the eggs.

The lung virus titer was expressed by mean ±SD. I some experiments, the lungs of 5 mice in a group were combined to prepare a lung suspension.

Incidence of Infection

Incidence of infection values were represented by the number of infected mice, in which the virus was present at $>10^1$ in the lung homogenate (10%), per 5 treated mice.

Statistics

Probability values were calculated by a student's t-test.

The following examples illustrate the present invention but are not to be construed as limiting:

EXAMPLE 2

Influenza HA Vaccine-CTB (Intranasal Preparation)

Influenza HA vaccine (1 mg HA/ml) and CTB, dissolved in PBS and aseptically filtered, were mixed to prepare the influenza HA vaccine-CTB, intranasal solution (20 μl) containing influenza HA vaccine (1.5-2 μg) and CTB (3.5-250 μg) together with added preservative and stabilizer, and filled into bottles. The vaccine preparation was stored in a cool dark place below 10°0 C. The effect of the vaccine preparation is illustrated hereinbefore.

EXAMPLE 3

Influenza HA Vaccine-CTB (Injection)

Influenza HA vaccine (1 mg HA/ml) and CTB, dissolved in PBS and aseptically filtered, were mixed to prepare the influenza HA vaccine-CTB, injectable solution (0.5 ml) containing influenza HA vaccine (1.5-2 μg) and CTB (2.5-250 μg) together with added preservative and stabilizer, and filled into vials. The vaccine preparation was stored in a cool dark place below 10° C. The effect of the vaccine preparation is illustrated hereinbefore.

EXAMPLE 4

Hepatitis B vaccine-CTB (Injection)

A hepatitis B vaccine-CTB for injection was prepared by mixing hepatitis B vaccine and CTB, dissolved in PBS and aseptically filtered, to prepare a mixture containing HBs antigen (40 μg protein) and CTB (2.5-250 μg) in 20 μl solution, together with added preservative and stabilizer, and filled into vials. The vaccine preparation was stored in a cool dark place below 10° C.

The thus-prepared hepatitis B vaccine preparation and CT were inoculated in mice and the serum titer 3 weeks after inoculation was measured.

As shown in the table immediately below, mice receiving hepatitis B vaccine showed a passive hemagglutination (PHA) titer of $2^{5.6}$ units and mice receiving additional CT showed a PHA titer of $2^{6.6}$ units, and hence antibodies production is seen to have been augmented.

TABLE

| Augmentation of Antibody Production by Adding CT to Hepatitis B Vaccine | |
|---|---|
| | Antibody titer PHA |
| CT | $2^{6.6}$ |
| No addition | $2^{5.6}$ |

The antibody titer was measured by the passive hemagglutination test. Antibody titers are expressed as the average of 5 mice.

EXAMPLE 5

Pertussis Vaccine-CTB (Intranasal)

Pertussis vaccine and CTB, dissolved in PBS and filtered aseptically, were mixed to prepare the intranasal pertussis vaccine-CTB by preparing a mixture of pertussis vaccine (14 μg protein nitrogen) and CTB (25-250 μg) in a volume of 20 μl, together with a preservative and a stabilizer and were stored in a bottle. The product was stored in a cool dark place below 10° C. CTB or CT was added to the pertussis vaccine 20 μl (13 μg protein nitrogen), and inoculated into mice intranasally. After 4 weeks, the same inoculum size of vaccine was administered intranasally to mice, and the antibodies titers were determined.

As shown in the immediately following table, the mice that received pertussis vaccine alone showed anti-PT antibodies of <4.1 units, and those receiving pertussis vaccine together with CTB or CT showed anti-PT antibodies of 140.3 units or 232.5 units, respectively. Anti-FHA antibodies of mice inoculated with vaccine alone, with added CTB or CT, were <2.6 units, <32.0 units and 43.9 units, respectively. Antibody production was augmented in mice when they were administered vaccine and CTB or CT.

TABLE

Augmentation of Antibody Production by Pertussis Vaccine with Added CT or CTB

| | Anti titer | |
|---|---|---|
| | anti PT | anti FHA |
| CT | 232.5 | 43.9 |
| CTB | 140.3 | 32.0 |
| No addition | <4.1 | <2.6 |

Titers: average of 5 mice
Titers: ELISA international unit

EXAMPLE 5

Diphtheria and Tetanus Toxoid Combined With Pertussis Vaccine-CTB (Intranasally)

A diphtheria and tetanus toxoid combined with pertussis vaccine-CTB intranasal preparation was prepared by mixing a diphtheria and tetanus toxoid combined with pertussis vaccine (hereinafter combined vaccine) with CTB dissolved in PBS and filtered aseptically, thus preparing a mixture (20 μl) of the combined vaccine (50 μg protein nitrogen) and CTB (2.5-250 μg), to which were added a preservative and a stabilizer, and the material was filled into a bottle.

The preparation was stored in a cool dark place below 10° C.

CTB was added to the combined vaccine, which was then inoculated into mice intranasally; and after 4 weeks there was further inoculated into the same mice the same size inoculum, and then the antibody titers were measured.

As shown in the immediately following table, mice receiving the combined vaccine alone showed anti-pertussis toxin (PT) antibodies <2.0 units, anti-diphtheria (DT) antibodies <1.5 unit and anti-tetanus toxoid (TT) <1.5 unit. Antibodies production, however was augmented by adding CTB, to 150.0, 110.5 and 120.0 units, respectively, as above.

TABLE

Augmentation of Antibody Production by Adding CTB to the Combined Vaccine

| Antigen: inoculum size | CTB | Antibody production ELISA-titer |
|---|---|---|
| Pertussis vaccine 14 μg | 5 μg | 150.0 |
| Diphtheria toxoid 16 μg | | 110.5 |
| Tetanus toxoid 15 μg | | 120.0 |
| Pertussis vaccine 14 μg | 0 μg | <2.0 |
| Diphtheria toxoid | | <1.5 |

TABLE-continued

Augmentation of Antibody Production by Adding CTB to the Combined Vaccine

| Antigen: inoculum size | CTB | Antibody production ELISA-titer |
|---|---|---|
| 16 μg | | |
| Tetanus toxoid 15 μg | | <1.5 |

Antibody titer: mean of 5 mice
Anti titer: ELISA I.U.

EXAMPLE 7

Japanese Encephalitis Vaccine-CTB (Injection)

A Japanese encephalitis vaccine-CTB (injection) was prepared by mixing Japanese encephalitis virus vaccine with CTB dissolved in PBS and filtering aseptically, preparing mixture (1 ml) of inactivated virus particles corresponding to Japanese encephalitis $10^{7.0}$ PFU and CTB (10.0–0 μg), adding preservative and a stabilizer, and filling into a vial.

The preparation was stored in a cool dark place below 10° C.

The Japanese encephalitis vaccine together with or without CTB or CT was inoculated into mice two times with a 1-week interval and the serum antibody titer was removed.

The neutralizing antibody titers of Japanese encephalitis virus with or without CTB or CT are $10^{1.88}$, $10^{2.58}$ and $>10^{3.20}$, respectively, and the antibody production was augmented by adding CTB or CT to the vaccine.

TABLE

Augmentation of Antibody Production by Adding CT or CTB to Japanese Encephalitis Vaccine

| | Concentration | Neutralizing titer $10^n$ |
|---|---|---|
| CT | 0.05 μg/Mouse | 3.39 |
| | 0.5 μg | 3.20 |
| | 5.0 μg | 3.52 |
| CTB | 0.05 μg/Mouse | 2.58 |
| | 0.5 μg | 2.70 |
| | 5.0 μg | 3.39 |
| no add. | | 1.88 |

Antibody titers of pooled serum of 10 mice

EXAMPLE 8

Measles Vaccine-CTB (Intranasal)

A measles vaccine-CTB intranasal preparation was prepared by mixing measles vaccine with CTB dissolved in PBS and filtering aseptically, preparing a mixture (20 μl) of virus particles corresponding to measles vaccine (20 μl) and CTB (5 μg), adding a preservative and a stabilizer, and filling into a bottle.

The preparation was stored in a cool dark place below 10° C.

The measles vaccine with or without CTB was inoculated two times into mice at 3-week intervals, and the serum antibody production was measured.

The ELISA antibody titer, as a result of administering measles vaccine alone, was 0.144, and that when CTB was added to the vaccine was >0.209. The augmentation of antibody production was thus observed when administering the vaccine with CTB.

TABLE

Augmentation of Antibody Production by
Adding CTB to Measles Vaccine

| Inoculum size | | Antibody production |
|---|---|---|
| Antigen | CTB | ELISA-titer |
| Measles vaccine 20 μg | 5 μg | 0.21 |
| Control 20 μg | 5 μg | 0.144 |

EXAMPLE

Rubella Vaccine-CTB (Intranasal)

A rubella vaccine-CTB intranasal preparation was prepared by mixing rubella vaccine with CTB dissolved in PBS and filtering aseptically, preparing a mixture (20 μl) of virus particles corresponding to rubella vaccine (20 μl) and CTB (5 μg), adding a preservative and a stabilizer, and filling into a bottle. The preparation was stored in a cool dark place 10° C.

The rubella vaccine with or without CTB was inoculated two times into mice at 3-week intervals, and the serum antibody production was measured.

The ELISA antibody titer, when rubella vaccine was administered alone, was 0.095, and that when CTB was added to the vaccine was >0.920. An augmentation of antibody production was thus observed when administering the vaccine with CTB.

TABLE

Augmentation of Antibody Production by
Adding CTB to Rubella Vaccine

| Inoculum size | | Antibody production |
|---|---|---|
| Antigen | CTB | ELISA-titer |
| Rubella vaccine 20 μg | 5 μg | 0.920 |
| Control 20 μg | 0 μg | 0.095 |

EXAMPLE 10

Mumps Vaccine-CTB (Intranasal)

A mumps vaccine-CTB intranasal preparation was prepared by mixing mumps vaccine with CTB dissolved in PBS and filtering aseptically, preparing a mixture (20 μl) of virus particles corresponding to mumps vaccine (20 μl) and CTB (5 μg), adding a preservative and a stabilizer, and filling into a bottle.

The preparation was stored in a cool dark place below 10° C. The mumps vaccine with or without CTB was inoculated two times into mice at 3-week intervals, and the serum antibody production was measured. The ELISA antibody titer, when mumps vaccine was administered alone, was 0.028, and that when CTB was added to the vaccine was >0.045. An augmentation of antibody production. was thus observed when administering the vaccine with CTB.

TABLE

Augmentation of Antibody Production by
Adding CTB to Mumps Vaccine

| Inoculum size | | Antibody production |
|---|---|---|
| Antigen | CTB | ELISA-titer |
| Mumps vaccine 20 μg | 5 μg | 0.05 |
| Control 20 μg | 0 μg | 0.028 |

EXAMPLE 11

Mixed Vaccine of Measles, Rubella and Mumps-CTB (Intranasal)

A mixed vaccine of measles, rubella and mumps-CTB intranasal preparation was prepared by mixing the mixed vaccine with CTB dissolved in PBS and filtering aseptically, preparing a mixture (20 μl) of virus particles corresponding to measles vaccine (7 μg), rubella vaccine (1 μg) and mumps vaccine (7 μg), and CTB (5 μg), adding a preservative and a stabilizer, and filling into a bottle.

The preparation was stored in a cool dark place below 10° C.

The vaccine with or without CTB was inoculated 2 times into mice at 3-week intervals, and the serum antibody production was measured.

The ELISA antibody titers, when administering the vaccine alone, were 0.14, 0.09 and 0.15, respectively, for measles, rubella and mumps, and those when CTB was added to the vaccine were 0.29, 0.30 and 0.24, respectively. An augmentation of antibody production was thus observed when administering the vaccine with CTB.

TABLE

Augmentation of Antibody Production by
Addition of CTB to the Mixed Vaccine of
Measles, Rubella and Mumps

| Inoculum size | | Antigen production |
|---|---|---|
| Antigen | CTB | ELISA-titer |
| Measles vaccine 7 μg | 5 μg | Measles 0.29 |
| Rubella vaccine 7 μg | | Rubella 0.30 |
| Mumps vaccine 7 μg | | Mumps 0.24 |
| Control | | Measles 0.14 |
| | | Rubella 0.09 |
| | | Mumps 1.15 |

EXAMPLE 12

Rota vaccine-CTB (oral and intranasal):

A rota vaccine-CTB oral and intranasal preparation was prepared by mixing rota vaccine with CTB dissolved in PBS and filtering aseptically, preparing a mixture (20 μl) of virus particles corresponding to rota vaccine (3.3 μl) and CTB (5 μg), adding a stabilizer, and filling into a bottle.

The preparation was stored in a cool dark place below 10° C.

The rota vaccine with or without CTB was inoculated two times into mice with a 3-week interval, and the serum antibody production was measured.

The ELISA antibody titer of the vaccine administered alone was 0.089 for intranasal administration, and that of the vaccine with CTB added was 0.281. For oral administration, the values were 0.018 and 0.277, respectively.

An augmentation of antibody production was observed when administering the vaccine with CTB.

TABLE

| Augmentation of Antibody Production by Addition of CTB of Rota Vaccine | | | |
|---|---|---|---|
| | Inoculum size | | Antibody Production |
| Antigen | | CTB | |
| Rota vaccine | | | |
| Intranasal | | | |
| Vaccine | 3.3 µg | 5 µg | 0.281 |
| Control | 3.3 µg | 0 µg | 0.089 |
| Oral | | | |
| Vaccine | 3.3 µg | 5 µg | 0.227 |
| Control | 3.3 µg | 0 µg | 0.018 |

EXAMPLE 13

Mycoplasma Vaccine-CTB (Injection)

A mycoplasma vaccine-CTB injectable preparation was prepared by mixing mycoplasma vaccine with CTB dissolved in PBS and filtering aseptically, preparing a mixture (1 ml) of mycoplasma corresponding to the vaccine ($2.0 \times 10^{10}$ CFU) (colony forming unit) and CTB (10 µg), adding a stabilizer, and filling into a vial. The preparation was stored in a cool dark place below 10° C. The vaccine with or without CTB was inoculated three times into chickens at 2-week intervals, and the number of lesions after mycoplasma infection was observed.

The administration of vaccine with CTB added shoed a marked protective effect as compared with the vaccine alone.

TABLE

| Decrease of Lesions After Mycoplasma Infection Upon Administering Mycoplasma Vaccine with CTB | | | |
|---|---|---|---|
| | Inoculum size | | |
| Antigen | | CTB | Lesion |
| Total mycoplasma cells*** | 5 µg | * | ** |
| $1.0 \times 10^{10}$ CFU | | 3/10 | 125 |
| Ultrasonication | 5 µg | 3/11 | 129 |
| $1.0 \times 10^{10}$ CFU | | | |
| Control | 0 µg | 10/10 | 277 |
| $1.0 \times 10^{10}$ CFU | | | |

*number of animals showing lesions/number of animals tested
**means value of lesions
***CFU

EXAMPLE 14

Pertussis Vaccine-LTB (intranasal)

A pertussis vaccine-LTB (intranasal) was prepared by mixing pertussis vaccine with LTB dissolved in PBS and filtering aseptically, preparing a mixture (20 µl) of pertussis vaccine (14 µg protein nitrogen) and LTB (2.5-250 µg), adding a preservative and a stabilizer, and filling into a bottle.

The preparation was stored in a cool dark place below 10° C.

LTB or LT was added to the pertussis vaccine 20 µl (13 µg protein nitrogen), and the mixture was inoculated into mice intranasally. After four weeks, the same inoculum size of vaccine was administered intranasally into the same mice, and the antibodies titers were determined.

As shown in the immediately following table, the mice receiving pertussis vaccine alone showed anti-PT antibodies in the number of <4.2 units, and those receiving pertussis vaccine together with CTB or CT showed anti-PT antibodies in the number of 150.3 units or 230.5 units, respectively. The anti-FHA antibodies of mice inoculated with vaccine alone, and with added CTB or CT were <2.3 units, <30.0 units and 40.5 units, respectively. Antibody production was thus seen to be augmented in mice when administering the vaccine and LTB or LT.

TABLE

| Augmentation of Antibody Production by Pertussis Vaccine with Added LT or LTB: | | |
|---|---|---|
| | Antibody titer | |
| | AntiPT | AntiFHA |
| LT | 230.5 | 40.5 |
| LTB | 150.3 | 30.0 |
| no add | <4.2 | <2.3 |

Antibody titer: mean of 5 mice
Antibody titer: ELISA I.U.

EXAMPLE 15

Diphtheria and Tetanus Toxoid Combined with Pertussis Vaccine-LTB (Intranasal):

A diphtheria and tetanus toxoid combined with pertussis vaccine-LTB intranasal preparation was prepared by mixing a diphtheria and tetanus toxoid combined with pertussis vaccine (hereinafter combined vaccine) with LTB dissolved in PBS and filtering aseptically, preparing a mixture (20 µl) of the combined vaccine (50 µg protein nitrogen) and LTB (2.5-250 µg), adding a preservative and a stabilizer, and filling into a bottle.

The preparation was stored in a cool dark place below 10° C.

LTB was added to the combined vaccine, and the mixture was inoculated into mice intranasally and after four weeks the same mice were again inoculated with the same inoculum size, and then the antibody titers were measured.

As shown in the table that follow immediately hereafter, the mice that received the combined vaccine alone showed anti-pertussis toxin (PT) and antibodies in the number of <1.8 I.U., anti-diphtheria (DT) antibodies <1.4 unit and anti-tetanus toxoid (TT) 1.2 unit. Antibodies production was thus seen to be augmented by a 0.3-fold addition of LTB, to 140.0, 80.5 and 100.5 I.U., respectively.

TABLE

| Augmentation of Antibody Production by Adding LTB to the Combined Vaccine | | |
|---|---|---|
| Antigen: Inoculum size | LTB | Antibody production ELISA-titer |
| Pertussis vaccine | 5 µg | |
| 14 µg | | 140.0 |
| Diphtheria toxoid | | |
| 16 µg | | 80.5 |
| Tetanus toxoid | | |
| 15 µg | | 100.2 |
| Pertussis vaccine | 0 µg | <1.8 |
| 14 µg | | |
| Diphtheria toxoid | | <1.4 |
| 16 µg | | |
| Tetanus toxoid | | <1.2 |
| 15 µg | | |

Antibody titer: mean of 5 mice
Antibody titer: ELISA I.U.

EXAMPLE 16

Rubella Vaccine-LTB (Intranasal)

A rubella vaccine-LTB intranasal preparation was prepared by mixing rubella vaccine with LTB dissolved in PBS and filtering aseptically, preparing a mixture (20 μl) of virus particles corresponding to rubella vaccine (3 μg) and LTB (5 μg), adding a stabilizer, and filling into a bottle. The preparation was stored in a cool dark place below 10° C. The rubella vaccine with or without LTB was inoculated two times into mice with a 3-week interval, and the serum antibody production was measured. The ELISA antibody titer when rubella vaccine was administered alone was 0.133, and that when LTB was added to the vaccine was >0.854. An augmentation of antibody production was thus observed when administering the vaccine with LTB.

TABLE

Augmentation of Antibody Production by an Addition of LTB to Rubella Vaccine

| Inoculum size | | Antibody production |
|---|---|---|
| Antigen | LTB | ELISA-titer |
| Rubella vaccine 3 μg | 5 μg | 0.854 |
| Control 3 μg | 0 μg | 0.133 |

EXAMPLE 17

Measles Vaccine-LTB (Intranasal)

A measles vaccine-LTB intranasal preparation was prepared by mixing measles vaccine with LTB dissolved in PBS and filtering aseptically, preparing a mixture (20 μl) of virus particles corresponding to measles vaccine (20 μg) and (5 μg), adding a stabilizer, and filling into a bottle.

The preparation was stored in a cool dark place below 10° C. The measles vaccine with or without LTB was inoculated two times into mice with a 3-week interval, and the serum antibody production was measured. The ELISA antibody titer when measles vaccine was administered alone was 0.182, and that when LTB was added to the vaccine was >0.332. An augmentation of antibody production was observed when administering the vaccine with LTB.

TABLE

Augmentation of Antibody Production by an Addition of LTB to Measles Vaccine

| Inoculum size | | Antibody production |
|---|---|---|
| Antigen | LTB | ELISA-titer |
| Measles vaccine 20 μg | 5 μg | 0.332 |
| Control 20 μg | 0 μg | 0.182 |

EXAMPLE 18

Mumps Vaccine-LTB (Intranasal)

A mumps vaccine-LTB intranasal preparation was prepared by mixing mumps vaccine with LTB dissolved in PBS and filtering aseptically, preparing a mixture (20 μl) of virus particles corresponding to mumps vaccine (20 μg) and (5 μg), adding a stabilizer, and filling into a bottle.

The preparation is stored in a cool dark place below 10° C. The mumps vaccine with or without LTB was inoculated two times into mice with a 3-week interval, and the serum antibody production was measured.

The ELISA antibody titer when measles vaccine was administered alone was 0.023, and that when LTB was added to the vaccine was 0.074. An augmentation of antibody production was thus observed when administering the vaccine with LTB.

TABLE

Augmentation of Antibody Production by an Addition of LTB to Mumps Vaccine

| Inoculum size | | Antibody production |
|---|---|---|
| Antigen | LTB | ELISA-titer |
| Mumps vaccine 20 μg | 5 μg | 0.074 |
| Control 20 μg | 0 μg | 0.023 |

EXAMPLE 19

Mixed Vaccine of Measles, Rubella and Mumps-LTB (Intranasal)

A mixed vaccine of measles, rubella and mumps-LTB intranasal preparation was prepared by mixing the mixed vaccine with LTB dissolved in PBS and filtering aseptically, preparing a mixture (20 μl) of virus particles corresponding to measles vaccine (7 μg), rubella vaccine (1 μg) and mumps vaccine (7 μg) and LTB (5 μg), adding a stabilizer, and filling into a bottle.

The preparation was stored in a cool dark place below 10°0 C.

The vaccine with or without LTB was inoculated two times into mice with a 3-week- interval, and the serum antibody production was measured.

The ELISA antibody titers when administering the vaccine alone were 0.18, 0.07 and 0.13, respectively for measles, rubella and mumps, and those when LTB was added to the vaccine were 0.34, 0.27 and 0.28, respectively. An augmentation of antibody production was thus observed when administering the vaccine with LTB.

TABLE

Augmentation of Antibody Production by an Addition of LTB to a Mixed Vaccine of Measles, Rubella and Mumps

| Inoculum size | | Antigen production | |
|---|---|---|---|
| Antigen | CTB | | ELISA-titer |
| Measles vaccine 7 μg | 5 μg | Measles | 0.34 |
| Rubella vaccine 7 μg | | Rubella | 0.27 |
| Mumps vaccine 7 μg | | Mumps | 0.28 |
| Control | 0 μg | Measles | 0.18 |
| | | Rubella | 0.07 |
| | | Mumps | 0.13 |

EXAMPLE 20

Rota Vaccine-LTB (Peroral and Intranasal)

A rota vaccine-LTB oral and intranasal preparation was prepared by mixing rota vaccine with LTB dissolved in PBS and filtering aseptically, preparing a mixture (20 μl) of virus particles corresponding to rota vaccine (3.3 μg) and LTB (5 μg), adding a stabilizer, and filling into a bottle.

The preparation was stored in a cool dark place below 10° C.

The rota vaccine with or without LTB was inoculated two times into mice with a 3-week interval, and the serum antibody production was measured.

The ELISA antibody titer when administering the vaccine alone was 0.063 for intranasal administration, and that when LTB was added to the vaccine was 0.348. These values were respectively 0.024 and 0.177 for oral administration.

An augmentation of antibody production was thus observed when administering the vaccine with LTB.

TABLE

Augmentation of Antibody Production by an Addition of LTB of Rota Vaccine

| Antigen | Inoculum size | LTB | Antibody Production |
|---|---|---|---|
| Rota vaccine |  |  |  |
| Intranasal |  |  |  |
| Vaccine | 3.3 µg | 5 µg | 0.348 |
| Control | 3.3 µg | 0 µg | 0.063 |
| Oral |  |  |  |
| Vaccine | 3.3 µg | 5 µg | 0.177 |
| Control | 3.3 µg | 0 µg | 0.024 |

EXAMPLE 21

Mycoplasma Vaccine-LTB (Injection)

A mycoplasma vaccine-lTB injectable preparation was prepared by mixing mycoplasma vaccine with LTB dissolved in PBS and filtering aseptically, preparing a mixture (1 ml) of mycoplasma corresponding to the vaccine ($2.0 \times 10^{10}$ CFU) (colony forming unit) and LTB (10 µg), adding a stabilizer, and filling into a vial.

The preparation was stored in a cool dark place below 10° C.

The vaccine with or without LTB was inoculated three times into chicken with a 2-week interval, and the number of lesions after the onset of mycoplasma infection was observed.

The administration of vaccine with LTB added showed a marked protective effect as compared with the vaccine alone.

TABLE

Decrease of Lesions After Mycoplasma Infection when Administering Mycoplasma Vaccine with LTB

| Antigen | Inoculum size LTB | Lesions | |
|---|---|---|---|
| Total mycoplasma cells*** $1.0 \times 10^{10}$ CFU | 5 µg | * 3/12 | ** 1.23 |
| Ultrasonication $1.0 \times 10^{10}$ CFU | 5 µg | 2/11 | 1.27 |
| Control $1.0 \times 10^{10}$ CFU | 0 µg | 10/10 | 2.77 |

*number of animals showing lesion/number of animals used
**mean of lesion/group
***CFU

What is claimed is:

1. A vaccine preparation comprising in combination a vaccine and a toxin or subunit thereof as an effective component, said toxin being a bacterial toxin selected from the group consisting of cholera toxin, staphylococcal α-hemolysin, staphylococcal α-hemolysin, vibrio thermostable direct hemolysin, pertussis toxin and E. coli heat-labile toxin, the ratio of vaccine to toxin or subunit thereof being 1.00001–1:10,000 (w/v).

2. A vaccine preparation according to claim 1 wherein the toxin is a B subunit or a part of a B subunit of a toxin.

3. A vaccine preparation according to claim 1 wherein the vaccine is selected from the group consisting of influenza vaccine, pertussis vaccine, Japanese encephalitis vaccine, mixed vaccine of pertussis, diphtheria and tetanus toxoid, hepatitis B vaccine, rota vaccine, measles vaccine, rubella vaccine, mumps vaccine, combined vaccine of measles, rubella and mumps, and mycoplasma vaccine.

4. A vaccine preparation according to claim 1 which is an intranasal vaccine.

5. A vaccine preparation according to claim 1 which is in injectable form.

6. A vaccine preparation according to claim 1 which is in spray form.

7. A vaccine preparation according to claim 1 which is in orally administrable form.

* * * * *

(12) REEXAMINATION CERTIFICATE (4448th)
United States Patent
Tamura et al.

(10) Number: US 5,182,109 C1
(45) Certificate Issued: Oct. 2, 2001

(54) VACCINE PREPARATION COMPRISING A BACTERIAL TOXIN ADJUVANT

(75) Inventors: Shinichi Tamura, Kanagawa; Takeshi Kurata, Tokyo; Chikara Aizawa; Takashi Nagamine, both of Kanagawa, all of (JP)

(73) Assignees: National Institute of Health; Kitasato Institute, both of Tokyo (JP)

Reexamination Request:
No. 90/004,367, Sep. 13, 1996

Reexamination Certificate for:
Patent No.: 5,182,109
Issued: Jan. 26, 1993
Appl. No.: 07/335,678
Filed: Apr. 10, 1989

(30) Foreign Application Priority Data

Apr. 8, 1988 (JP) .................................. 63-86693
Jan. 13, 1989 (JP) .................................. 1-6759

(51) Int. Cl.$^7$ .......................... A61K 39/02; A61K 39/12
(52) U.S. Cl. ............................ 424/197.11; 424/192.1; 424/193.1; 424/234.1; 424/184.1; 424/236.1; 424/257.1; 424/261.1
(58) Field of Search ...................... 424/184.1, 236.1, 424/257.1, 241.1, 237.1, 261.1, 197.1

(56) References Cited

U.S. PATENT DOCUMENTS 5,079,165 * 1/1992 Clements et al. .................. 435/252.8
5,137,721 * 8/1992 Dallas ...................................... 424/93

FOREIGN PATENT DOCUMENTS

8606635 * 11/1986 (WO) .......................... A61K/39/385

OTHER PUBLICATIONS

J. Clements et al., "Adjuvant activity of *Escherichia coli* heat–labile enterotoxin and effect on the induction of oral tolerance in mice to unrelated protein antigens", Vaccine, Jun. 1988, vol. 6, pp. 269–277.

Nedrud et al Journal of Immunology 139: 3484–3492, 1987.*

Mitchell et al Aust. J. Exp. Biol Med Sci. 61: 425–434, 1983.*

Liang et al Journal of Immunology 141: 1495–1501, 1988.*

Tamura et al Vaccine 6: 409–413, 1988.*

Clements et al Immunopharmacology of Infectious Diseases: Vaccine Adjuvants and Modulators of Non–Specific Resistance, pp. 139–154, 1987.*

Svennerholm et al The Journal of Infectious Diseases 149:884–893, 1984.*

Takeda et al Saishin Igaku 43:474–478 (Abstract Only), 1988.*

Klipstein et al Development of Vaccines and Drugs Against Diarrhea pp. 62–67, 1986, (Abstract Only).*

* cited by examiner

*Primary Examiner*—Rodney P. Swartz

(57) ABSTRACT

A vaccine preparation comprising in combination a vaccine and a toxin or subunit thereof as an effective component. The toxin is preferably a bacterial toxin, e.g. cholera toxin, staphylococcal α-hemolysin, staphylococcal δ-hemolysin, vibrio thermostable direct hemolysin pertussis toxin or *E. coli* heat-labile toxin. The toxin can be a B subunit or a part of a B subunit of a toxin. The vaccine can be influenza vaccine, pertussis vaccine, Japanese encephalitis vaccine, mixed vaccine of pertussis, diphtheria and tetanus toxoid, hepatitis B vaccine, rota vaccine, measles vaccine, rubella vaccine, mumps vaccine, combined vaccine of measles, rubella and mumps, or mycoplasma vaccine. The ratio of vaccine to toxin or subunit thereof is 1:0.0001–1:10,000 (w/v). The vaccine can be intranasal vaccine, or can be in injectable form, spray form or oral administration form.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–7, dependent on an amended claim, are determined to be patentable.

New claims 8–15 are added and determined to be patentable.

1. A vaccine preparation [comprising in combination] *consisting essentially of a mixture of* a vaccine and [a] *an isolated* toxin or subunit thereof as an effective component, said toxin being a bacterial toxin *unrelated to said vaccine and* selected from the group consisting of [cholera toxin,] staphylococcal α-hemolysin, staphylococcal δ-hemolysin, *and* vibrio thermostable direct hemolysin, [pertussis toxin and E. coli heat-labile toxin,] the ratio of vaccine to toxin or subunit thereof being [1.00001–1:10,000] *1:0.0001–1:10,000* (w/v).

8. *A vaccine preparation consisting essentially of a mixture of a vaccine other than cholera vaccine and an isolated B subunit or a part of a B subunit of cholera toxin, the ratio of vaccine to said B subunit or part thereof being 1:0.0001–1:10,000 (w/v).*

9. *A vaccine preparation according to claim 8 wherein the vaccine is selected from the group consisting of pertussis vaccine, Japanese encephalitis vaccine, mixed vaccine of pertussis, diphtheria and tetanus toxoid, hepatitis B vaccine, rota vaccine, measles vaccine, rubella vaccine, mumps vaccine, combined vaccine of measles, rubella and mumps, and mycoplasma vaccine.*

10. *A vaccine preparation according to claim 8 which is an intranasal vaccine.*

11. *A vaccine preparation according to claim 8 which is in injectable form.*

12. *A vaccine preparation according to claim 8 which is in spray form.*

13. *A vaccine preparation according to claim 8 which is in orally administrable form.*

14. *A vaccine preparation according to claim 8 wherein the vaccine is influenza vaccine.*

15. *A vaccine preparation consisting essentially of a mixture of a vaccine other than pertussis vaccine and an isolated B subunit or a part of a B subunit of pertussis toxin, the ratio of vaccine to said B subunit or part thereof being 1:0.0001–1:10,000 (w/v).*

* * * * *